(12) United States Patent
Kwon et al.

(10) Patent No.: US 9,330,440 B2
(45) Date of Patent: May 3, 2016

(54) MEDICAL IMAGE PROCESSING APPARATUS AND METHOD FOR SYNTHESIZING AND DISPLAYING MEDICAL IMAGE GENERATED USING MULTI-ENERGY X-RAY

(71) Applicant: SAMSUNG ELECTRONICS CO., LTD., Suwon-si (KR)

(72) Inventors: Jae Hyun Kwon, Hwaseong-si (KR); Sung Su Kim, Yongin-si (KR); Young Hun Sung, Hwaseong-si (KR); Hyun Hwa Oh, Hwaseong-si (KR); Myung Jin Chung, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 7 days.

(21) Appl. No.: 13/955,475

(22) Filed: Jul. 31, 2013

(65) Prior Publication Data

US 2014/0119668 A1    May 1, 2014

(30) Foreign Application Priority Data

Oct. 31, 2012    (KR) .......................... 10-2012-0121796

(51) Int. Cl.
 *G06T 11/00*    (2006.01)
 *G06T 5/00*    (2006.01)
 (Continued)

(52) U.S. Cl.
 CPC ................. *G06T 5/002* (2013.01); *A61B 6/463* (2013.01); *A61B 6/482* (2013.01); *A61B 6/5205* (2013.01); *A61B 6/5235* (2013.01); *G06T 5/50* (2013.01); *G06T 11/005* (2013.01); *A61B 6/4007* (2013.01); *A61B 6/4241* (2013.01); *A61B 6/502* (2013.01);*G06T 2207/10116* (2013.01); *G06T 2211/408* (2013.01)

(58) Field of Classification Search
 CPC ................... A61B 6/482; A61B 6/502; G06T 2207/10116; G06T 2207/30068; G06T 2207/30096; A61N 2005/1061; G01N 2223/423; H05G 1/60
 USPC .................................................. 382/132, 232
 See application file for complete search history.

(56) References Cited

U.S. PATENT DOCUMENTS

| 2003/0158470 | A1* | 8/2003 | Wolters et al. ................ 600/317 |
| 2004/0022359 | A1 | 2/2004 | Acharya et al. |
| 2004/0064037 | A1* | 4/2004 | Smith ........................... 600/420 |

(Continued)

FOREIGN PATENT DOCUMENTS

| JP | 2005-046267 A | 2/2005 |
| JP | 2009-261519 A | 11/2009 |

(Continued)

OTHER PUBLICATIONS

U.S. Appl. No. 61/662,029, filed Jun. 20, 2012; Wang et al.; Specification pp. 1-15; Drawing pp. 1-7; Claims pp. 1-3.*

*Primary Examiner* — Kim Vu
*Assistant Examiner* — Michael Vanchy, Jr.
(74) *Attorney, Agent, or Firm* — Sughrue Mion, PLLC

(57) ABSTRACT

A medical image processing apparatus may include an image data generator to generate image data corresponding to at least two different energy bands by using an X-ray, an ROI processor to highlight a tissue of interest classified based on a predetermined characteristic to be distinguished from a normal tissue, in the generated image data, and a display to alternately display first image data in which the tissue of interest is not highlighted, and second image data in which the tissue of interest is highlighted to be distinguished from the normal tissue.

9 Claims, 17 Drawing Sheets

(51) Int. Cl.
*G06T 5/50* (2006.01)
*A61B 6/00* (2006.01)

(56) References Cited

U.S. PATENT DOCUMENTS

2009/0296884 A1 12/2009 Honda et al.
2011/0301447 A1* 12/2011 Park et al. .................... 600/407
2012/0063662 A1* 3/2012 Kwon et al. ................... 382/132
2012/0101733 A1* 4/2012 Han et al. ........................ 702/19
2013/0342577 A1* 12/2013 Wang et al. ................... 345/634

FOREIGN PATENT DOCUMENTS

KR 10-2004-0047561 A 6/2004
KR 10-2011-0080532 A 7/2011

* cited by examiner

200

300

900

EXAMPLE OF FULL SPECTRUM OF MEX SYSTEM

EXAMPLE OF LOW/MID/HIGH SPECTRUM OF MEX SYSTEM

RESOLUTION
IMPROVEMENT
PROCESSED
IMAGE

REGION OF
INTEREST
IMAGE

IMPROVED
INTEREST-
HIGHLIGHTED
SYNTHESIS
IMAGE

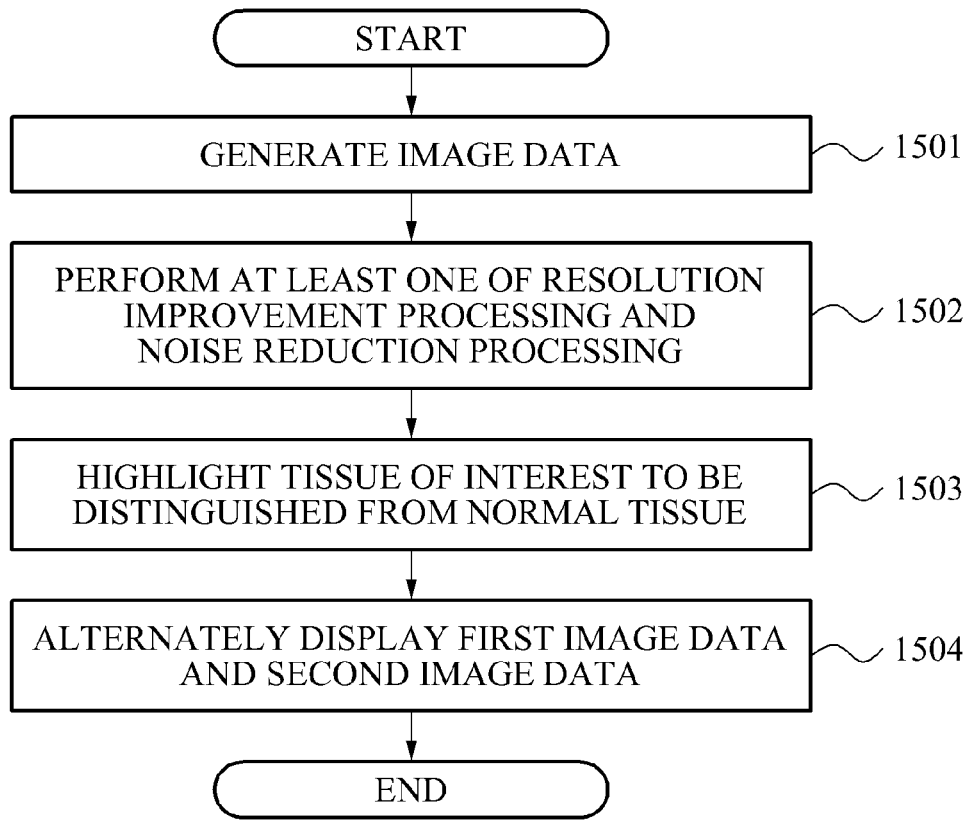

MEDICAL IMAGE PROCESSING APPARATUS AND METHOD FOR SYNTHESIZING AND DISPLAYING MEDICAL IMAGE GENERATED USING MULTI-ENERGY X-RAY

CROSS-REFERENCE TO RELATED APPLICATION

This application claims priority from Korean Patent Application No. 10-2012-0121796, filed on Oct. 31, 2012, in the Korean Intellectual Property Office, the entire disclosure of which is incorporated herein by reference.

BACKGROUND

1. Field

Methods and apparatuses consistent with exemplary embodiments relate to imaging an object by using multi-energy X-rays, and displaying the images for a diagnosis to be made.

2. Description of the Related Art

X-rays are widely used in various fields to acquire medical information related to a patient at a hospital, and the like.

The X-rays are generated when electrons generated by a cathode filament strike an anode target. When the generated X-rays are irradiated to an object, the X-rays may be attenuated based on a material or a characteristic of the object, and X-rays passing through the object may form an image on a detector installed behind the object.

A large number of X-ray systems may display images using an attenuation characteristic detected when X-rays having a single energy band pass through an object. In such X-ray systems, when materials constituting the object have different attenuation characteristics, an image with good quality may be acquired. However, when the materials have similar attenuation characteristics, a quality of the image may be deteriorated.

A system using multi-energy X-ray (MEX) may acquire an X-ray image of at least two energy bands. In general, a material may have different X-ray attenuation characteristics in different energy bands. Accordingly, such characteristics may be used for decomposing an image for each material.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

According to an aspect of an exemplary embodiment, there is provided a medical image processing apparatus, including an image data generator to generate a plurality of image data corresponding to at least two different energy bands with respect to an object, using an X-ray, a region of interest (ROI) processor to highlight a tissue of interest classified based on a predetermined characteristic to be distinguished from a normal tissue, with respect to the generated plurality of image data, and a display to alternately display first image data in which the tissue of interest is not highlighted, and second image data in which the tissue of interest is highlighted, among the plurality of image data, based on a predetermined criterion.

According to an aspect of an exemplary embodiment, there is provided a medical image processing apparatus, including an image data generator to generate a plurality of image data corresponding to at least two different energy bands with respect to an object comprising a region of interest, using a wide-band energy X-ray, a resolution improvement and noise reduction processor to perform at least one of a resolution improvement processing and a noise reduction processing, with respect to the plurality of image data, respectively, a first synthesis image generator to generate first image data, by synthesizing the plurality of image data on which at least one of the resolution improvement processing and the noise reduction processing is performed respectively, a spectral image generator to generate second image data, by synthesizing the plurality of image data on which the at least one of the resolution improvement processing and the noise reduction processing is performed respectively, and converting the synthesized image data into a color image, and a display to alternately display the first image data and the second image data, based on a predetermined criterion.

According to an aspect of an exemplary embodiment, there is provided a medical image processing method, including generating a plurality of image data in a plurality of energy bands with respect to an object, using a wide-band energy X-ray, performing at least one of a resolution improvement processing and a noise reduction processing, with respect to the generated plurality of image data, highlighting a tissue of interest classified based on a predetermined characteristic to be distinguished from a normal tissue, with respect to the generated plurality of image data, and alternately displaying first image data in which the tissue of interest is not highlighted, and second image data in which the tissue of interest is highlighted, among the plurality of image data, based on a predetermined criterion.

BRIEF DESCRIPTION OF THE DRAWINGS

The above and/or other aspects will become more apparent by describing certain exemplary embodiments, with reference to the accompanying drawings, in which:

FIG. 15 is a flowchart illustrating a medical image processing method according to an exemplary embodiment.

DETAILED DESCRIPTION

Figure 1:
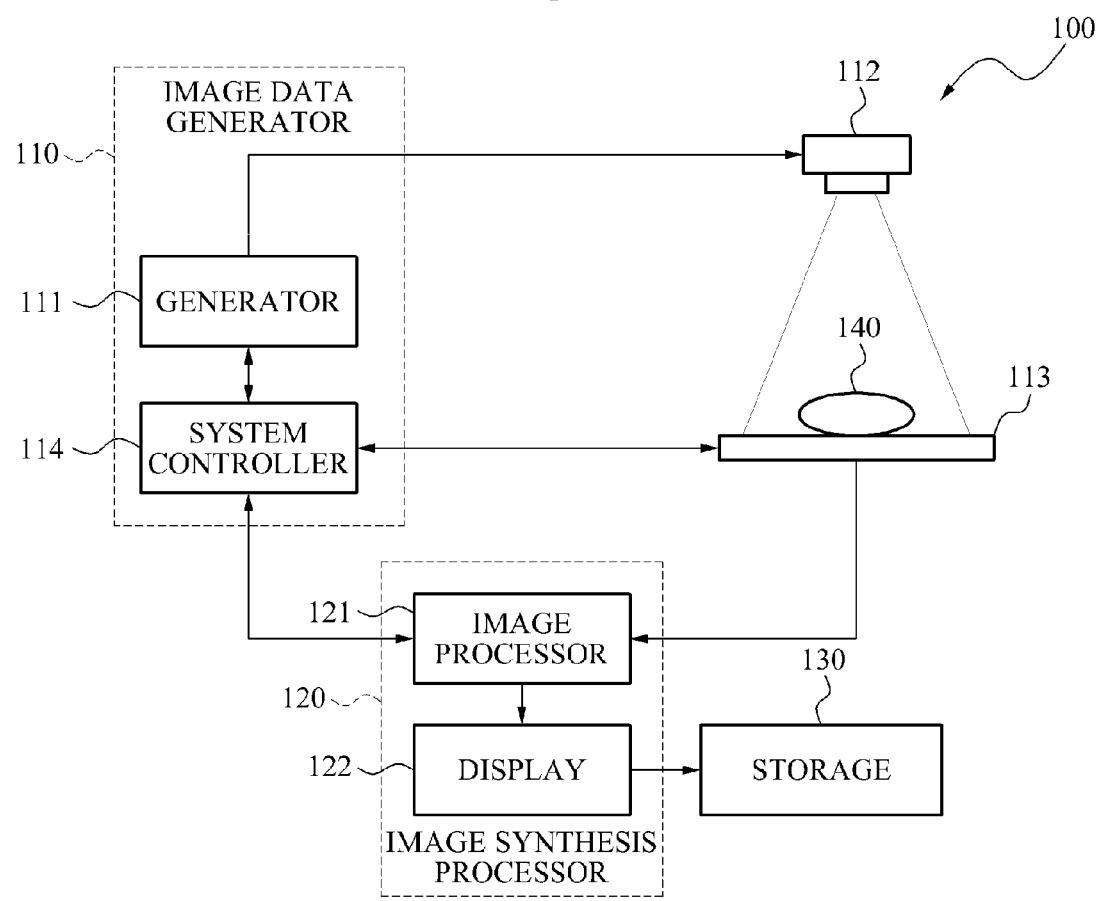
FIG. 1 is a diagram illustrating a medical image processing apparatus according to an exemplary embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

MEX imaging is a technology in which a contrast between materials is increased using a difference in absorption characteristics of human body materials changing based on energy. Related art MEX technologies may be classified into a multiple exposure technique, and a single exposure technique.

In a multiple exposure technique, a MEX image may be acquired by exposing X-rays having different X-ray spectrums, sequentially. To this end, by changing an anode target of a source, a material/thickness of a filter, a tube voltage of an X-ray tube, and the like, a shape of an X-ray spectrum, a position of centroid energy, or the like may be changed.

As a difference in energies of an acquired image increases, a contrast of an X-ray image may be increased through a MEX image analysis, for example, an energy subtraction. Accordingly, in order to acquire a high quality X-ray image, proper selection of a type of an anode target, a material of a filter, a tube voltage, and the like may be required to minimize a change in energy and an overlap phenomenon.

However, a time difference caused by a sequential exposure may result in a motion artifact, an increase in an image acquisition time, and the like.

Accordingly, when the multiple exposure technique is used for a medical X-ray, certain restraints may exist.

In contrast to the multiple exposure technique, a MEX image may be acquired at a single exposure, in the single exposure technique.

To this end, an X-ray source may generate a single wide spectrum, for example, a tungsten target of 50 kilovolt peaks (kVp), and a detector may identify energies of an incident X-ray photon, whereby images for each energy may be acquired simultaneously.

The detector capable of identifying energies may include a photon counting detector, a dual layer detector, a filter array detector, and the like.

The single exposure technique may differ from the multiple exposure technique in that a plurality of MEX images may be acquired simultaneously and, thus, the single exposure technique may reduce an image acquisition time and occurrence of motion artifacts resulting from a time difference of the multiple exposure technique.

FIG. 1 is a diagram illustrating a medical image processing apparatus 100 according to an exemplary embodiment.

The apparatus 100 may acquire a plurality of X-ray image data of different energy bands, and process an image. In this manner, the apparatus 100 may enhance a contrast of a tissue of interest.

Referring to FIG. 1, the apparatus 100 may include an image data generator 110, and an image synthesis processor 120.

The image data generator 110 may generate image data of at least two different energy bands with respect to an object, using an X-ray.

The image data generator 110 may include a generator 111, and a system controller 114.

The generator 111 may generate a MEX, and the X-ray tube 112 may irradiate the generated MEX to an object 140.

The generator 111 may adjust a voltage, for example, a tube voltage corresponding to kVp, applied to a cathode of the X-ray tube 112. In this instance, thermoelectrons emitted from the cathode may collide with an anode material in the X-ray tube 112, and the X-ray may be emitted.

An X-ray energy spectrum may be adjusted based on a tube voltage applied to the cathode, a type and a thickness of a filter in front of an anode. The X-ray may be irradiated toward the object, and may be detected by the X-ray detector 113.

For example, the generator 111 may generate a wide-band energy spectrum X-ray having energy of about 10 to 50 kiloelectron volts (keV), for example, in a case of mammography, and irradiate the X-ray to the object. The X-ray detector 113 may separate and detect the X-ray based on a number of predetermined energy thresholds, thereby generating a plurality of X-ray energy images.

The X-ray detector 113 may acquire a MEX generated when the irradiated X-ray passes through the object 140, thereby generating the plurality of image data.

For example, the X-ray detector 113 may include a photon-counting detector (PCD) capable of dividing an X-ray spectrum into a plurality of partial bands, and detecting the X-ray for each band, and may acquire image data of different energy bands simultaneously.

The system controller 114 may control at least one of the generator 111, the X-ray tube 112, and the X-ray detector 113.

The image synthesis processor 120 may highlight a tissue of interest classified based on a predetermined characteristic to be distinguished from a normal tissue, with respect to a portion of the generated plurality of image data.

The image synthesis processor 120 may include an image processor 121, and a display 122.

For example, the image processor 121 may generate first image data, and second image data in which the tissue of interest classified based on the predetermined characteristic is highlighted to be distinguished from the normal tissue, with respect to the generated plurality of image data.

In this instance, the display 122 may alternately display the first image data in which the tissue of interest is not highlighted, and the second image data in which the tissue of interest is highlighted, among the plurality of image data, based on a predetermined criterion.

For example, the display 122 may alternately display the first image data and the second image data, and display each of the first image data and the second image data once.

The image processor 121 may generate the first image data, by performing at least one of a resolution improvement processing and a noise reduction processing with respect to the generated plurality of image data.

For example, the image processor 121 may generate the first image data, by performing at least one of the resolution improvement processing and the noise reduction processing with respect to the generated plurality of image data, and synthesizing a plurality of image data on which at least one of the resolution improvement processing and the noise reduction processing is performed.

In particular, the image processor 121 may generate a high quality medical image by increasing a resolution and reducing noise based on a characteristic for each X-ray energy level, thereby generating an image having a characteristic similar to a characteristic of a related art mammogram image.

In addition, the apparatus 100 may generate a synthesis image in which a tissue of interest has a characteristic similar to a characteristic of a mass.

In particular, the image processor 121 may generate the second image data, by highlighting the tissue of interest to be distinguished from the normal tissue, with respect to a portion of the generated plurality of image data.

For example, the image processor 121 may highlight the tissue of interest to be distinguished from the normal tissue, with respect to a portion of the first image data.

The tissue of interest may refer to a body tissue in which a lesion occurs, and may be distinguished from an ordinary normal tissue without a lesion. The tissue of interest may be construed to be a mass tissue.

The display 122 may alternately display the first image data in which the tissue of interest is not highlighted, and the second image data in which the tissue of interest is highlighted, based on a predetermined criterion.

The image processor 121 may generate a single image, by synthesizing the first image data on which the resolution improvement processing and the noise reduction processing are performed with the second image data in which the tissue of interest is highlighted. In this instance, the second image data may be synthesized after the tissue of interest is highlighted in grayscale or after the tissue of interest is converted in color, depending on a type and a purpose of the display 122.

When the tissue of interest is highlighted in grayscale, the image processor 121 may express the tissue of interest with a relatively high brightness value to highlight the tissue of interest.

When the tissue of interest is highlighted in color, the image processor 121 may highlight the tissue of interest using a color different from a color used for the normal tissue.

The display 122 may alternately display the first image data similar to the related art mammogram image, and the second image data in which the tissue of interest is highlighted in grayscale or in color.

The apparatus 100 may further include a storage 130 to share the generated first image data and second image data with another entity over a network, or to store the generated first image data and second image data in a predetermined storage space.

Figure 2:
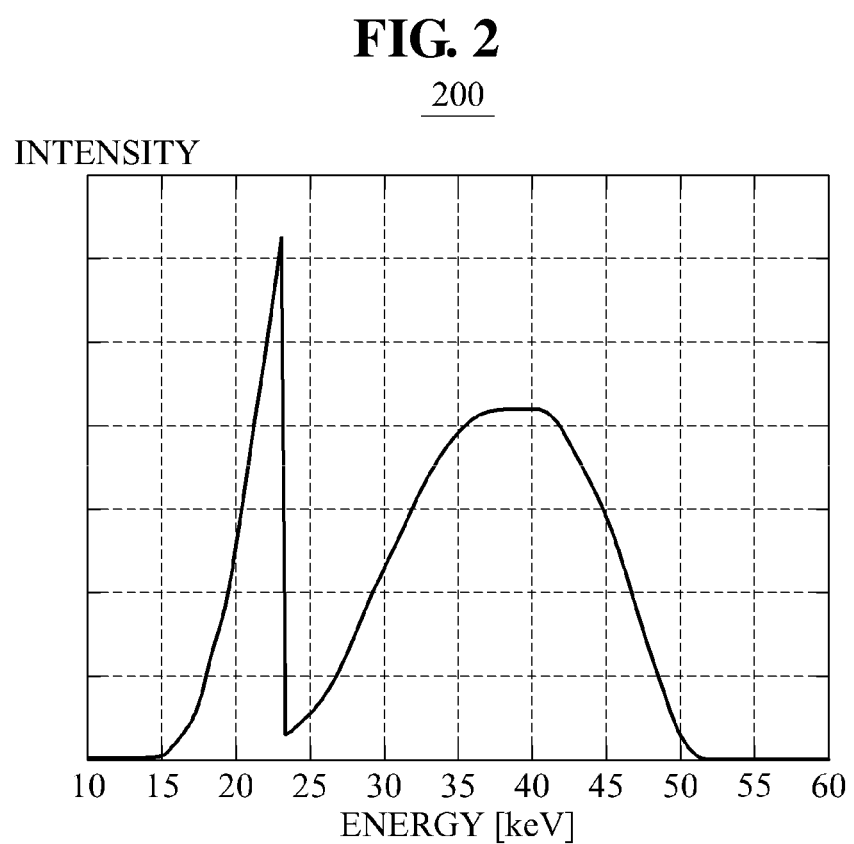
FIG. 2 is a graph illustrating a full energy spectrum capable of being generated by a medical image processing apparatus according to an exemplary embodiment.
Figure 3:
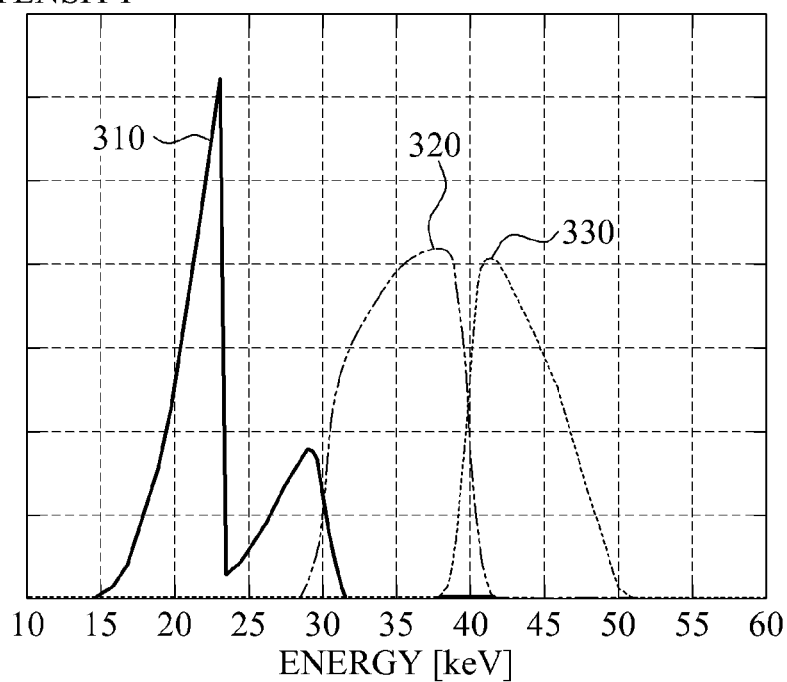
FIG. 3 is a graph illustrating an energy spectrum divided into three partial bands capable of being generated by a medical image processing apparatus according to an exemplary embodiment.

FIG. 2 is a graph illustrating a full energy spectrum capable of being generated by a medical image processing apparatus according to an exemplary embodiment, and FIG. 3 is a graph illustrating an energy spectrum divided into three partial bands capable of being generated by a medical image processing apparatus according to an exemplary embodiment.

FIG. 2 illustrates an example of a full X-ray energy spectrum 200. The medical image processing apparatus may detect an X-ray for each energy band, using a photon-counting detector.

In mammography, when a full X-ray energy spectrum ranging from about 15 keV to about 50 keV is acquired and divided into three partial bands, a low-energy spectrum 310, a mid-energy spectrum 320, and a high-energy spectrum 330 may be acquired, as shown in FIG. 3. In addition, an energy threshold distinguishing each partial band may be variable depending on imaging condition and purpose.

In the medical image processing apparatus, an energy band used for each application may be variable, and image data of each partial band may have a certain meaning. According to the present exemplary embodiment, X-ray image data of a plurality of different energy bands may be acquired and processed, whereby a contrast of a tissue of interest may be enhanced.

Figure 4:
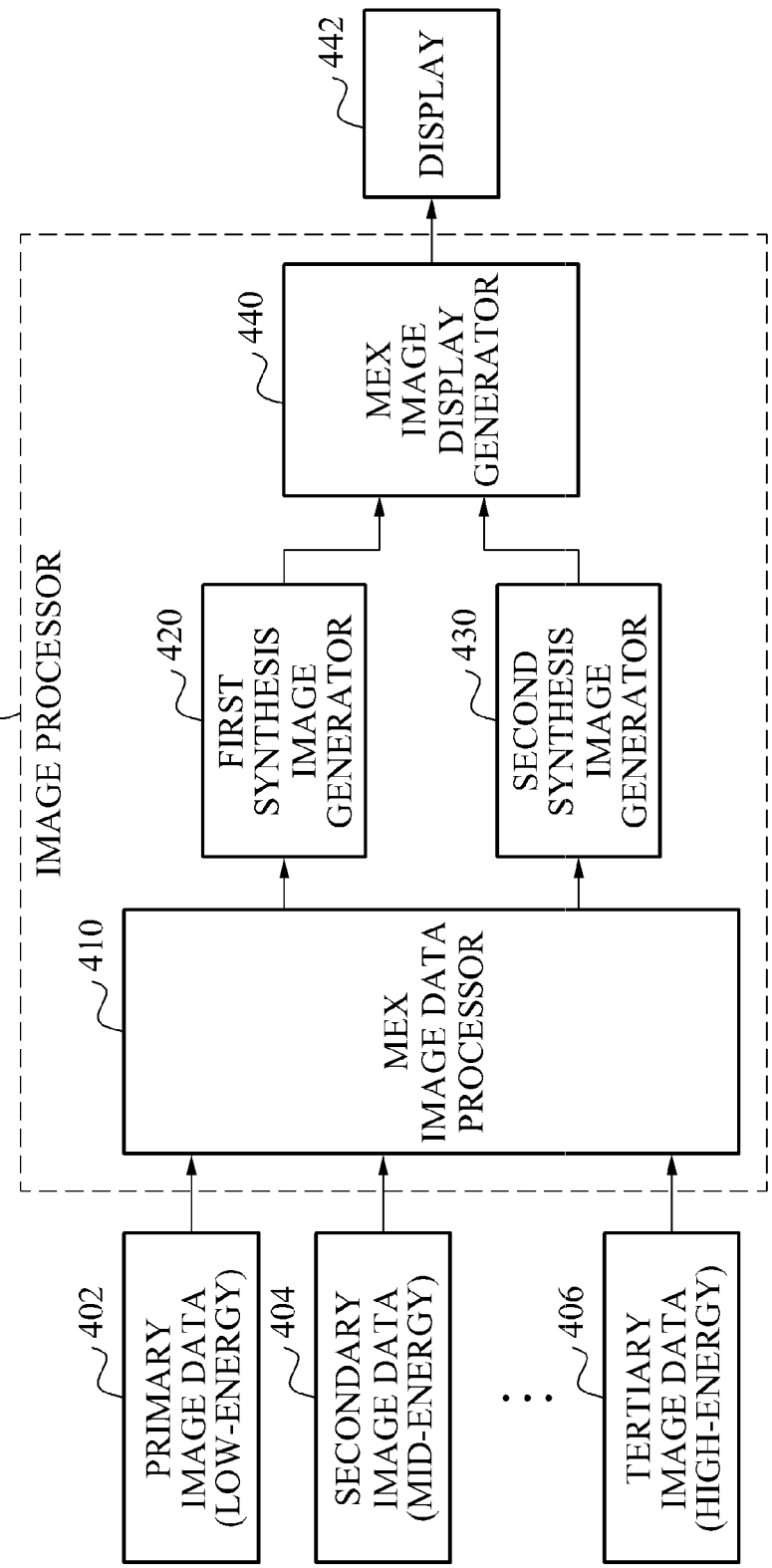
FIG. 4 is a block diagram illustrating an image processor of a medical image processing apparatus according to an exemplary embodiment.

FIG. 4 is a block diagram illustrating an image processor 400 of a medical image processing apparatus according to an exemplary embodiment.

Referring to FIG. 4, the image processor 400 may include a MEX image data processor 410, a first synthesis image generator 420, a second synthesis image generator 430, and a MEX image display generator 440.

The MEX image data processor 410 may receive an input of a plurality of image data generated by an image data generator.

For example, the MEX image data processor 410 may receive an input of low-energy image data 402 as primary image data, mid-energy image data 404 as secondary image data, and high-energy image data 406 as tertiary image data. Although data of three energy bands are illustrated, the MEX image data processor 410 may receive an input of fewer or more sets of data of different energy bands.

The MEX image data processor 410 may generate a high quality medical image, through a process of increasing details of the plurality of image data, removing noise from the plurality of image data, and the like, based on a characteristic for each X-ray energy band.

The first synthesis image generator 420 may generate first image data having a characteristic similar to a characteristic of a related art mammogram image using a single energy, with respect to the generated high quality medical image, and the second synthesis image generator 430 may generate second image data in which a tissue of interest having a characteristic similar to a characteristic of a mass is highlighted.

The MEX image display generator 440 may control a display 442 to alternately display the first image data and the second image data.

Figure 5:
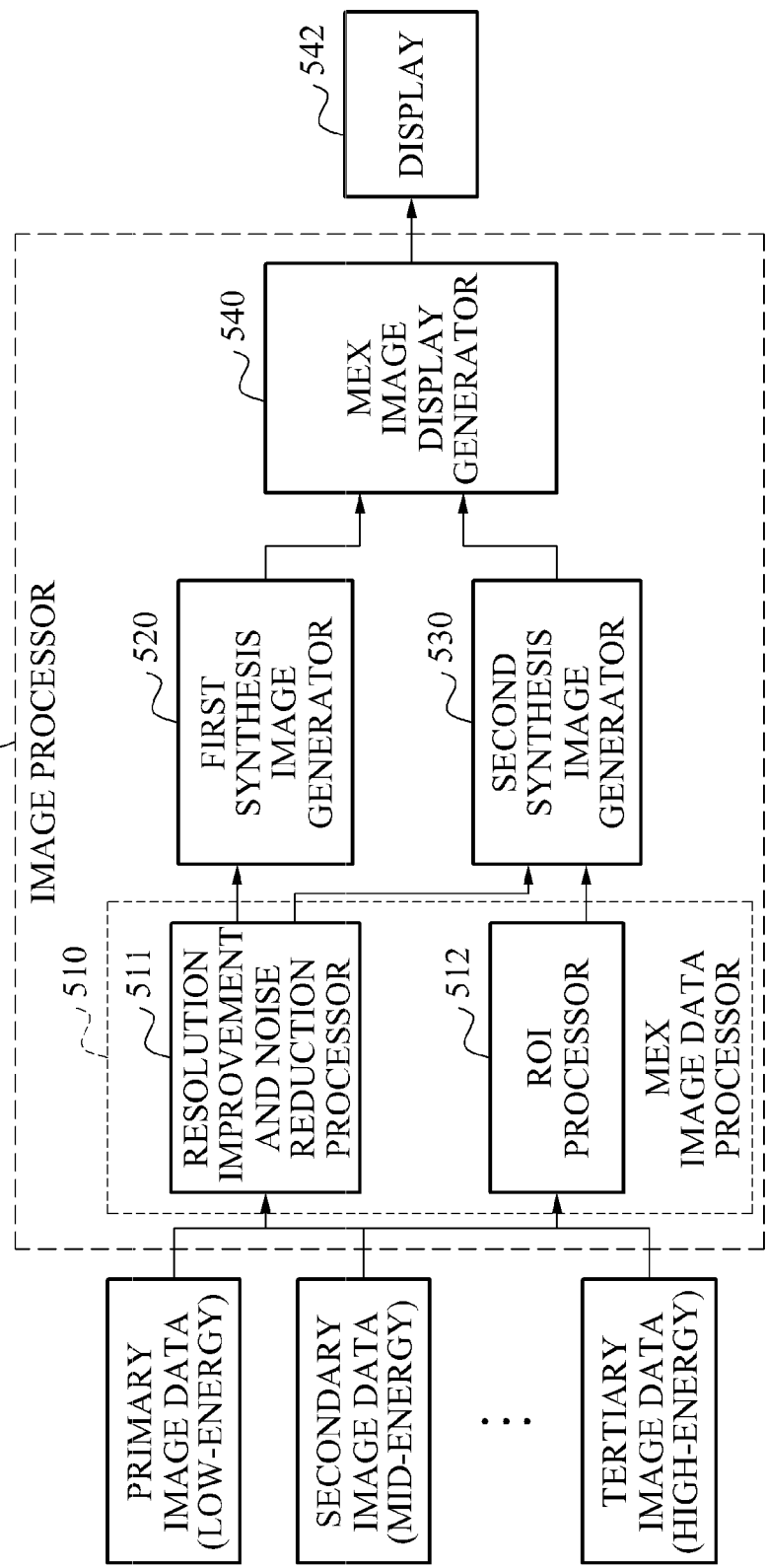
FIG. 5 is a block diagram illustrating a detailed configuration of an image processor of a medical image processing apparatus according to an exemplary embodiment.

FIG. 5 is a block diagram illustrating a detailed configuration of an image processor 500 of a medical image processing apparatus according to an exemplary embodiment.

The MEX image data processor 410 of FIG. 4 will be described in detail with reference to FIG. 5.

A MEX image data processor 510 may include a resolution improvement and noise reduction processor 511, and an ROI processor 512.

The MEX image data processor 510 may generate a high quality medical image, by increasing details of a plurality of image data based on a characteristic for each X-ray energy band through the resolution improvement and noise reduction processor 511 increasing a resolution of the plurality of image data or reducing noise from the plurality of image data.

In addition, the ROI processor 512 may generate image data in which a tissue of interest having a characteristic similar to a characteristic of a mass is highlighted in comparison to a normal tissue.

A first synthesis image generator 520 may correspond to the first synthesis image generator 420 of FIG. 4. The first synthesis image generator 520 may generate first image data by synthesizing image data in which a resolution is increased and an amount of noise is reduced.

Accordingly, the first synthesis image generator 520 may generate the first image data having a characteristic similar to a characteristic of a related art mammogram image using a single energy.

In addition, a second synthesis image generator 530 may correspond to the second synthesis image generator 430 of FIG. 4. The second synthesis image generator 530 may generate second image data, by synthesizing a plurality of image data on which at least one of a resolution improvement processing and a noise reduction processing is performed with a plurality of image data in which the tissue of interest is highlighted.

For example, the second synthesis image generator 530 may generate the second image data, using an output of the ROI processor 512 and an output of the resolution improvement and noise reduction processor 511. Accordingly, the tissue of interest may be highlighted, and high quality second image data may be generated.

A MEX image display generator 540 may control the first image data and the second image data to be displayed alternately on a display 542. For example, display 542 may display a grayscale image. For example, the MEX image display generator 540 may control the display based on predetermined criteria, for example, a number of times each of the first image data and the second image data is to be displayed, a period for which each of the first image data and the second image data is to be displayed, a display time, and the like.

The ROI processor 512 may change a brightness of the tissue of interest such that the tissue of interest is highlighted in comparison to the normal tissue.

In particular, the ROI processor 512 may highlight the tissue of interest in grayscale to generate the second image data.

Figure 6:
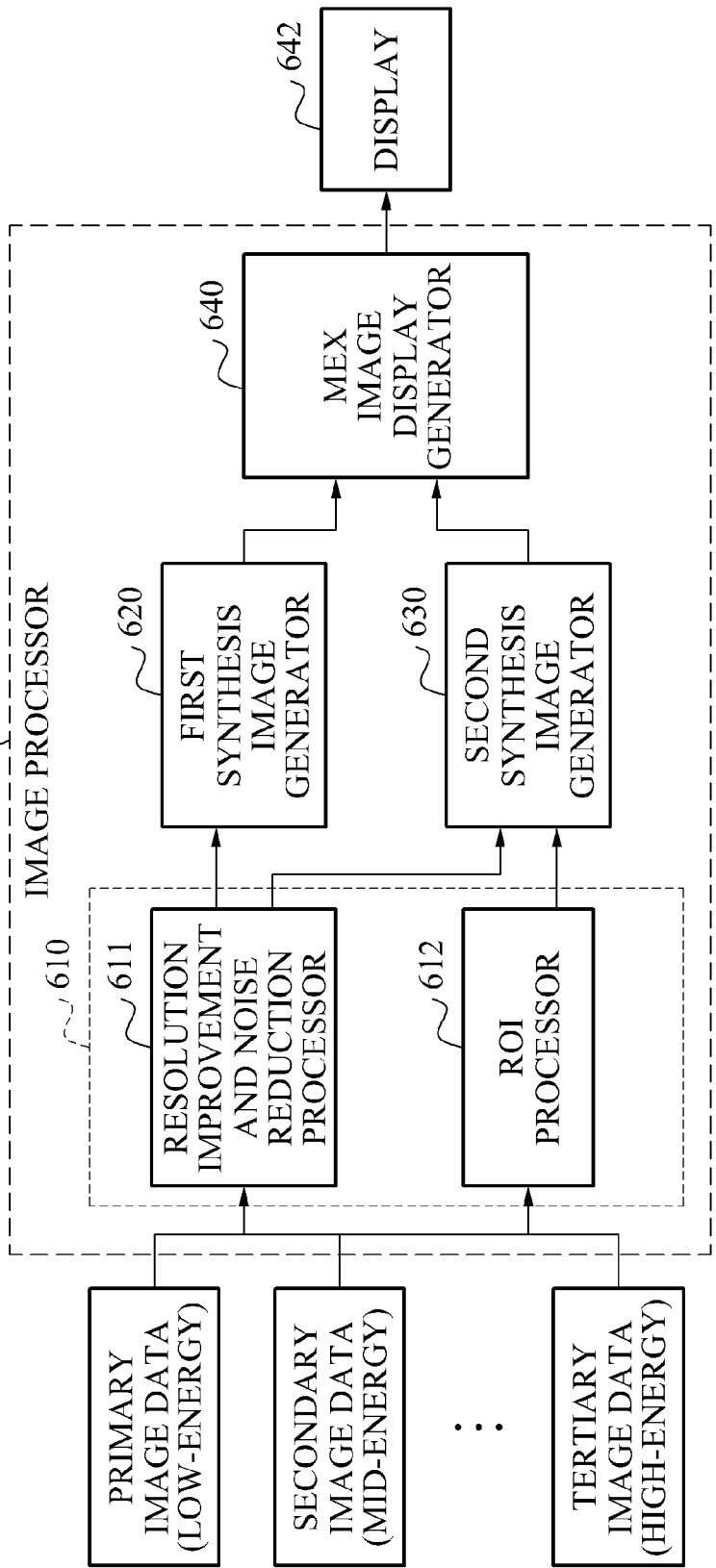
FIG. 6 is a block diagram illustrating a detailed configuration of an image processor of a medical image processing apparatus according to an exemplary embodiment.

FIG. 6 is a block diagram illustrating a detailed configuration of an image processor 600 of a medical image processing apparatus according to an exemplary embodiment.

In an image synthesis process, second image data in which a tissue of interest is highlighted in grayscale may be generated. In this instance, the tissue of interest may be highlighted by expressing the tissue of interest with a relatively high brightness value. As another example, the tissue of interest may be highlighted using a color in the image synthesis process.

A second synthesis image generator 630 may express a tissue of interest corresponding to a mass in color, rather than in grayscale. A MEX image display generator 640 may display a resolution-improved synthesis image and a tissue of interest synthesis image on a display, and may control the display to alternately output the resolution-improved synthesis image and the tissue of interest synthesis in grayscale or in color, depending on a type and purpose of the display.

For example, referring to FIG. 6, a MEX image data processor 610 may include a resolution improvement and noise reduction processor 611, and an ROI processor 612.

The resolution improvement and noise reduction processor 611 may increase details of a plurality of image data based on a characteristic for each X-ray energy band by increasing a resolution of the plurality of image data or reducing noise, thereby generating a high quality medical image. In addition, the ROI processor 612 may generate color image data in which a tissue of interest having a characteristic similar to a characteristic of a mass is highlighted in color, in comparison to a normal tissue.

A first synthesis image generator 620 may generate first image data, by synthesizing image data in which a resolution is increased and an amount of noise is reduced.

In addition, the second synthesis image generator 630 may generate second image date, by synthesizing a plurality of image data on which at least one of a resolution improvement processing and a noise reduction processing is performed with a plurality of image data in which the tissue of interest is highlighted in color.

For example, the second synthesis image generator 630 may generate the second image data, using an output of the ROI processor 612 and an output of the resolution improvement and noise reduction processor 611. Accordingly, the tissue of interest may be highlighted, and high quality second image data may be generated.

The MEX image display generator 640 may control the first image data and the second image data to be displayed alternately on the display 642. For example, the display 642 may display a color image. For example, the MEX image display generator 640 may control the display based on predetermined criteria, for example, a number of times each of the first image data and the second image data is to be displayed, a period over which each of the first image data and the second image data is to be displayed, a display time, and the like.

Figure 7:
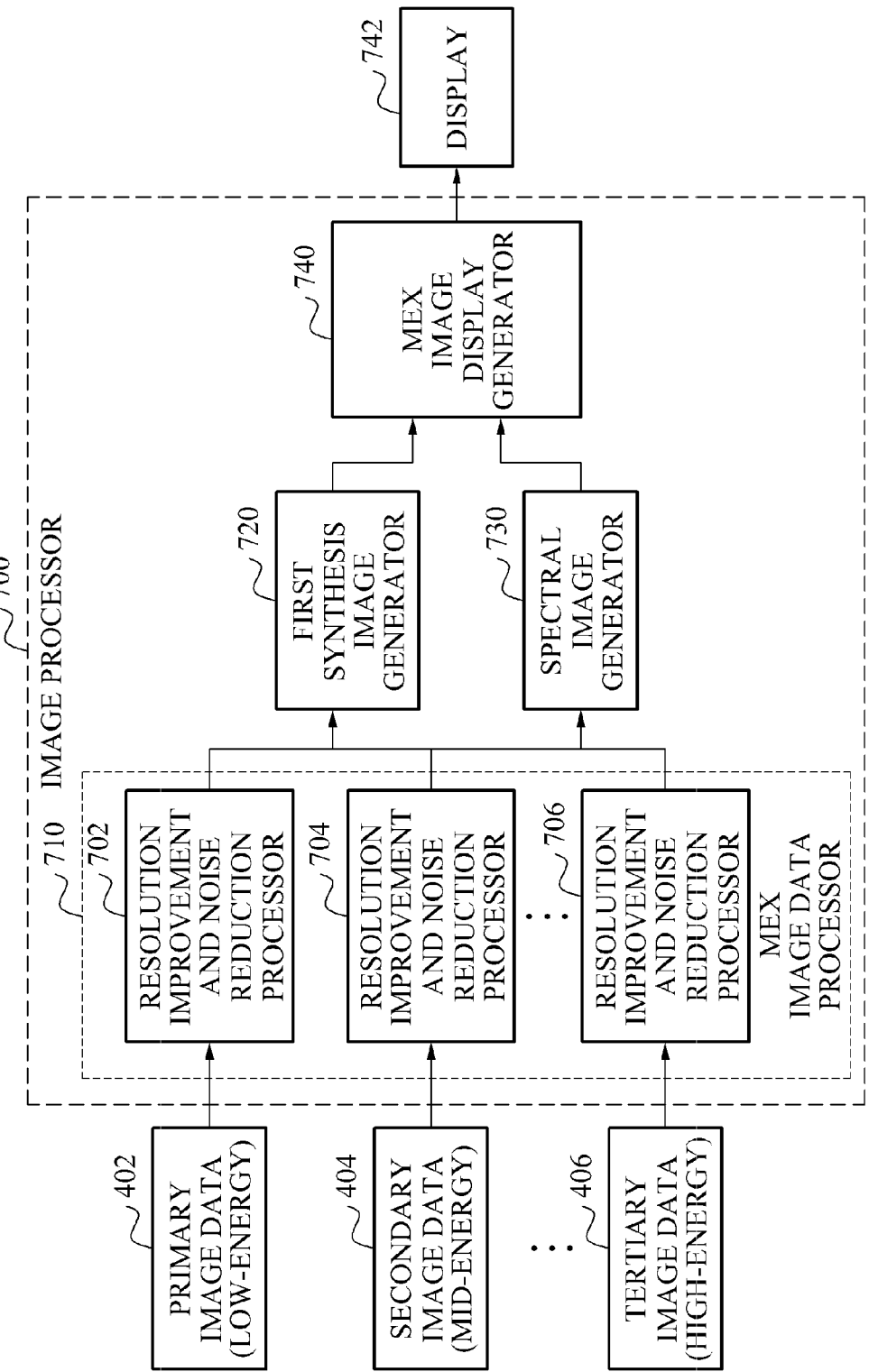
FIG. 7 is a block diagram illustrating a detailed configuration of an image processor of a medical image processing apparatus generating a spectral image according to an exemplary embodiment.

FIG. 7 is a block diagram illustrating a detailed configuration of an image processor 700 of a medical image processing apparatus generating a spectral image according to an exemplary embodiment.

As another example of a MEX image data processor 710 constituting the image processor 700, resolution improvement and noise reduction processors 702 and 704 to 706 included in the MEX image data processor 710 may perform a contrast and details improvement processing and a noise reduction processing, with respect to a plurality of image data corresponding to an output of an image data generator, respectively.

A first synthesis image generator 720 may generate first image data, by synthesizing a plurality of image data output by the respective resolution improvement and noise reduction processors.

A spectral image generator 730 may generate a color image by synthesizing the plurality of image data output by the respective resolution improvement and noise reduction processors.

For example, when the MEX image data processor 710 receives image data divided into three spectrums, for example, low-energy image data 402, mid-energy image data 404, and high-energy image data 406, the image data may be generated into color images having a red value, a green value, and a blue value in a sequential order, based on a low energy band.

In this instance, a weight of a channel may be variable depending on an energy band.

A MEX image display generator 740 may control a display 742 to display spectral image data generated into the color image.

The MEX image display generator 740 may alternately display the first image data generated in grayscale by the first synthesis image generator 720, and second image data as a spectral image expressed in color.

Each input may be converted into multi-scale and multi-directional information, by a second synthesis image generator, through a wavelet transform, a curvelet transform, a contourlet transform, or the like.

Figure 8:
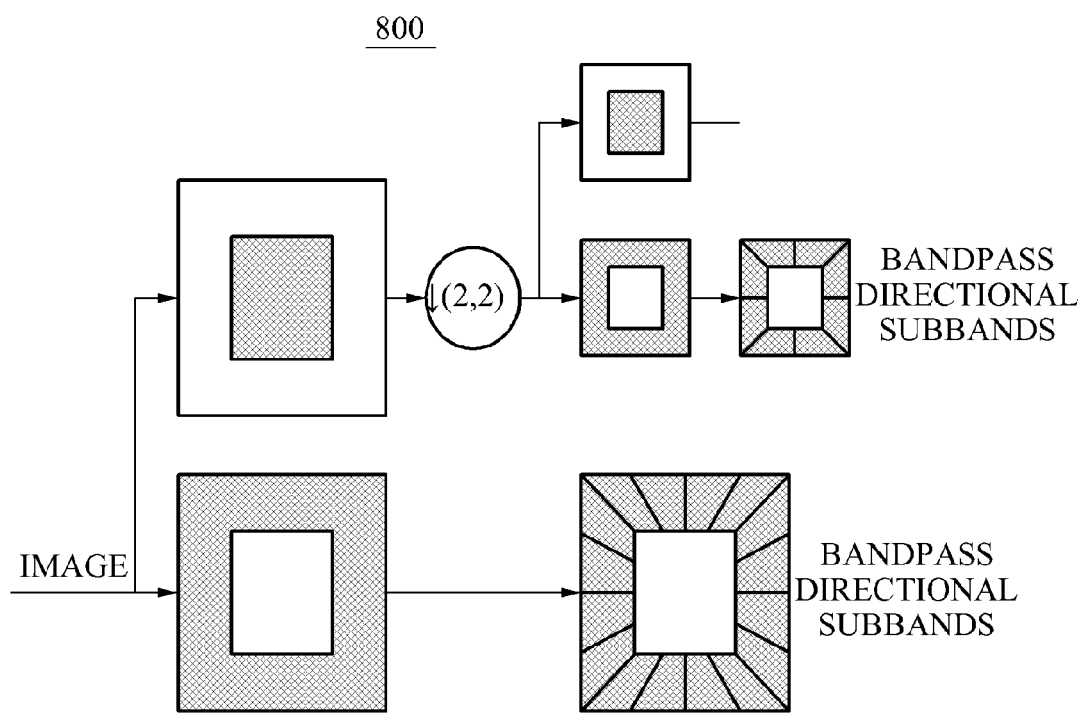
FIG. 8 is a diagram illustrating a contourlet transform performed by a tissue of interest synthesis image generator according to an exemplary embodiment.

FIG. 8 is a diagram 800 illustrating a contourlet transform performed by a second synthesis image generator according to an exemplary embodiment.

As shown in FIG. 8, the contourlet transform may extract more directional information than a wavelet transform and thus, may effectively process a smooth contour.

In addition, the contourlet transform may be implemented in a double filter structure of a Laplacian pyramid and a directional filter bank.

In order to prevent occurrence of an artifact, for example, a pseudo-Gibbs phenomenon, around an edge, maintenance of a shift-invariant characteristic may be needed. To this end, the contourlet transform may be implemented in an over-complete technique, without a sampling process.

Figure 9:
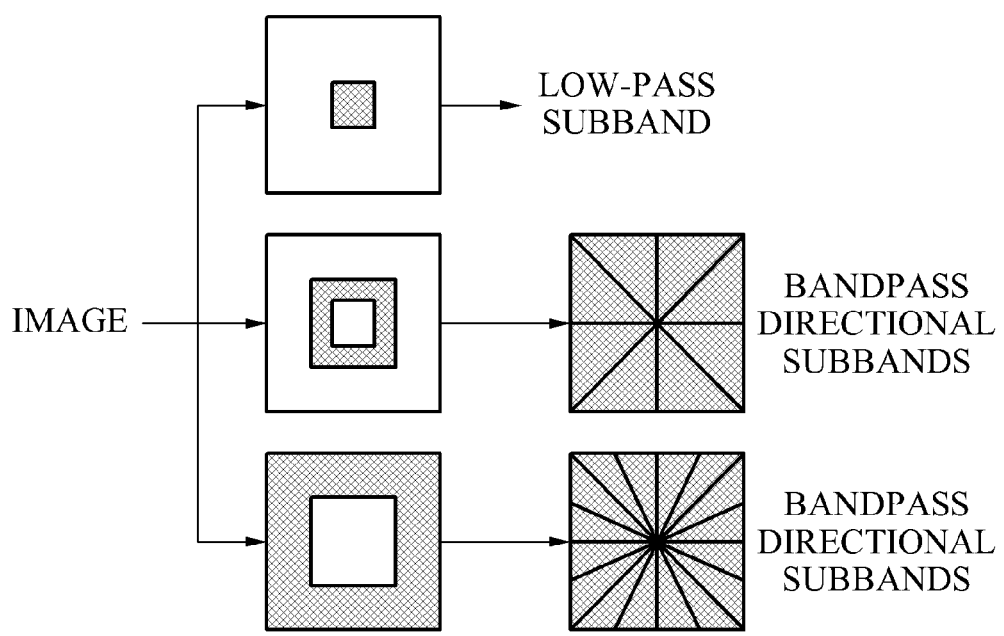
FIG. 9 is a diagram illustrating a non-subsampled contourlet transform (NSCT) performed by a tissue of interest synthesis image generator according to an exemplary embodiment.

FIG. 9 is a diagram 900 illustrating nonsubsampled contourlet transform (NSCT) performed by a second synthesis image generator according to an exemplary embodiment.

An ROI image and a resolution improvement and noise reduction processed image input from the second synthesis image generator may be decomposed into multi-scale and multi-directional information, through a contourlet transform. In this instance, a resolution of a low-pass image may be determined based on a decomposition level, and edge information to be extracted may be changed based on a number of directions and a type of a directional filter.

In particular, the second synthesis image generator may generate second image data, by multi-scaling a plurality of image data on which at least one of a resolution improvement processing and a noise reduction processing is performed, and a plurality of image data in which a tissue of interest is highlighted, respectively, converting the multi-scaled image data into multi-directional information, performing at least one of a coefficient synthesis of a low-pass component and a coefficient synthesis of a high-pass component, with respect to the image data converted into the multi-directional information, and reconstructing a result of the synthesizing through inverse contourlet transform (ICT).

For example, the second synthesis image generator may generate the second image data, by applying a weight to the low-pass component on a pixel basis.

Figure 10:
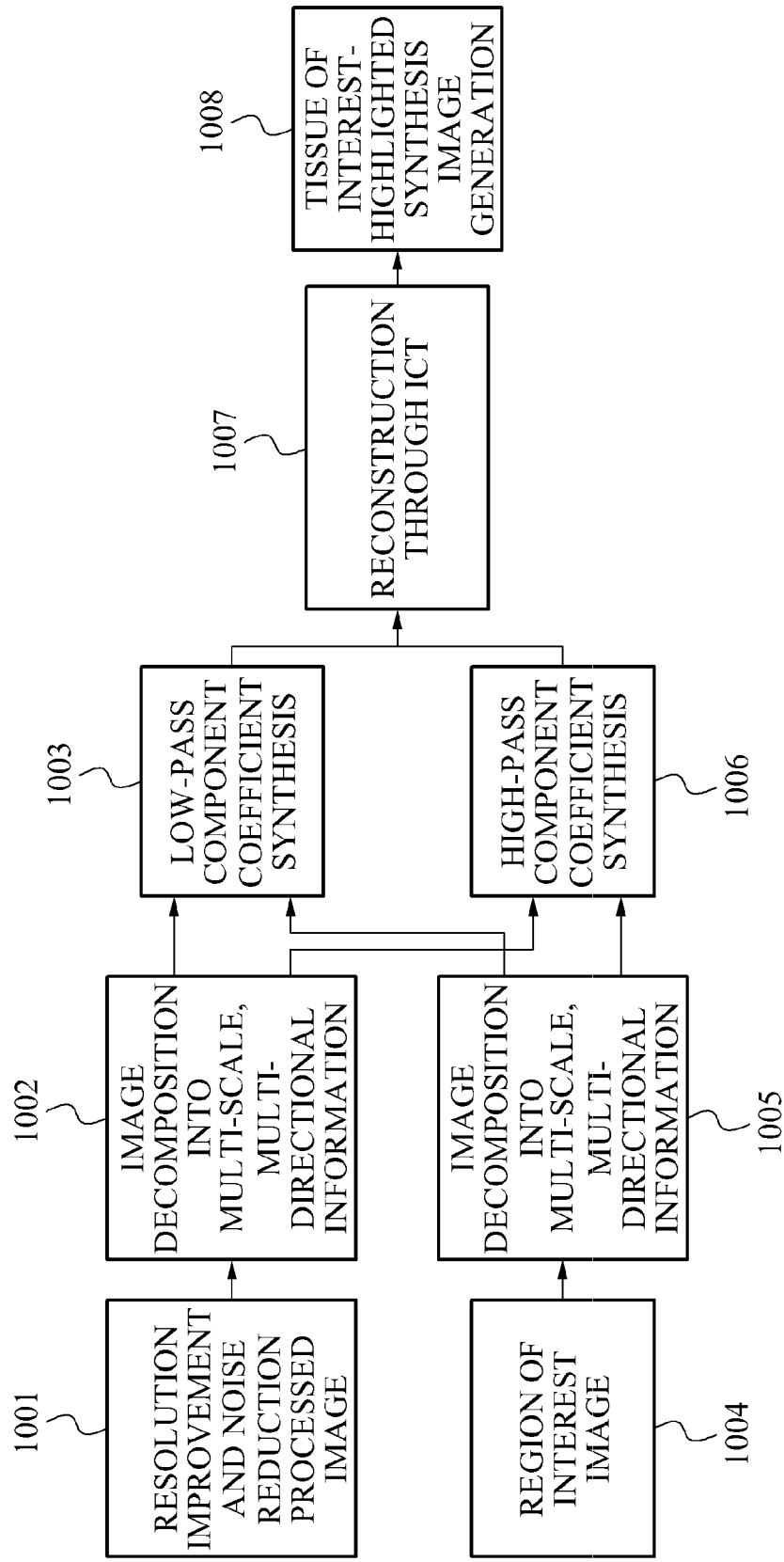
FIG. 10 is a diagram illustrating an image processing process of a tissue of interest synthesis image generator according to an exemplary embodiment.

FIG. 10 is a diagram illustrating an image processing process of a second synthesis image generator according to an exemplary embodiment.

Referring to FIG. 10, coefficients of a low-pass subband and bandpass directional subbands may be synthesized, respectively, and may be generated into a final tissue of interest-highlighted synthesis image through ICT.

For example, the second synthesis image generator may decompose an input resolution improvement and noise reduction processed image 1001 and an input ROI image 1004 in which a tissue of interest is highlighted, into multi-scale and multi-directional information through contourlet transform in operations 1002 and 1005, respectively.

The second synthesis image generator may synthesize the multi-directional information decomposed after the resolution improvement processing and noise reduction processing are performed, and the ROI image 1004 in which the tissue of interest is highlighted, with a coefficient of a low-pass component in operation 1003 and with a coefficient of a high-pass component in operation 1006, perform ICT reconstruction in operation 1007, and generate the final tissue of interest-highlighted synthesis image in operation 1008.

Figure 11:
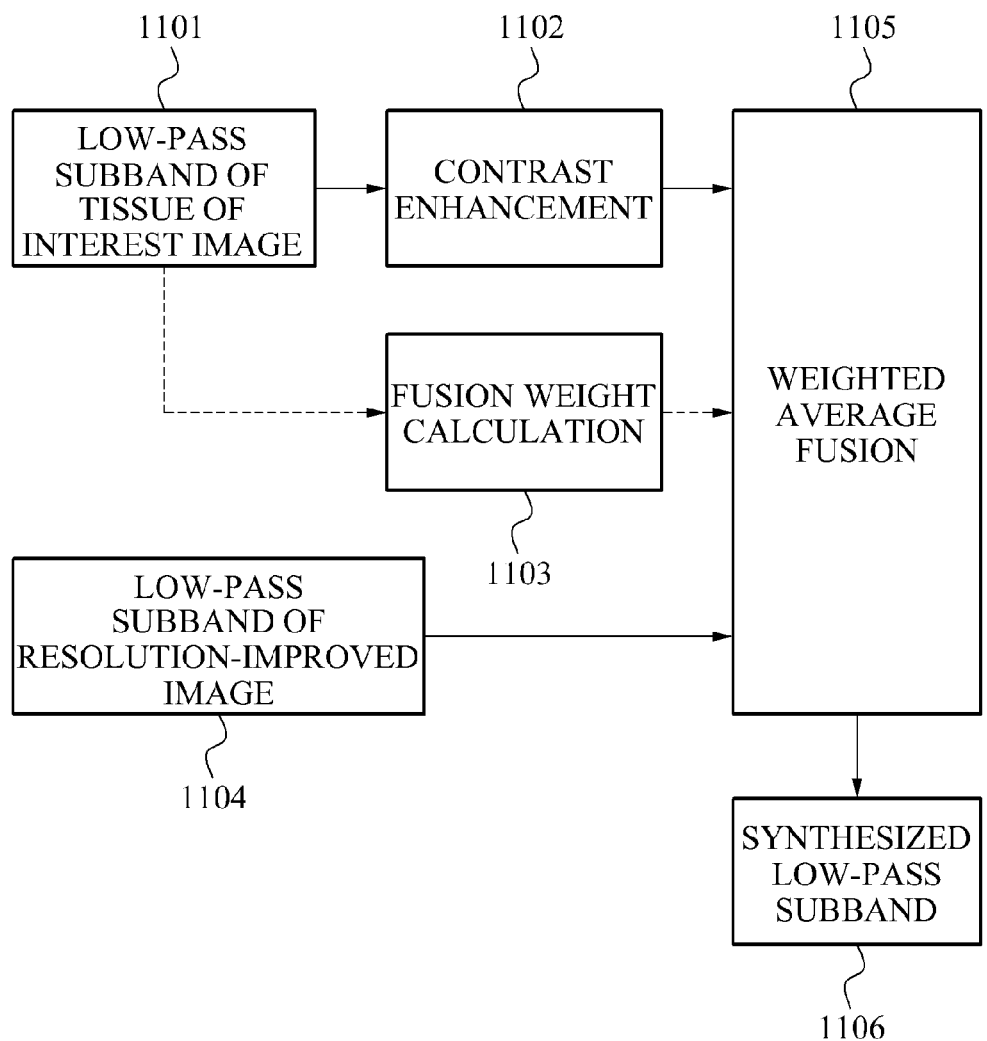
FIG. 11 is a diagram illustrating a process of a tissue of interest synthesis image generator synthesizing a coefficient of a low-pass component according to an exemplary embodiment.
Figure 12:
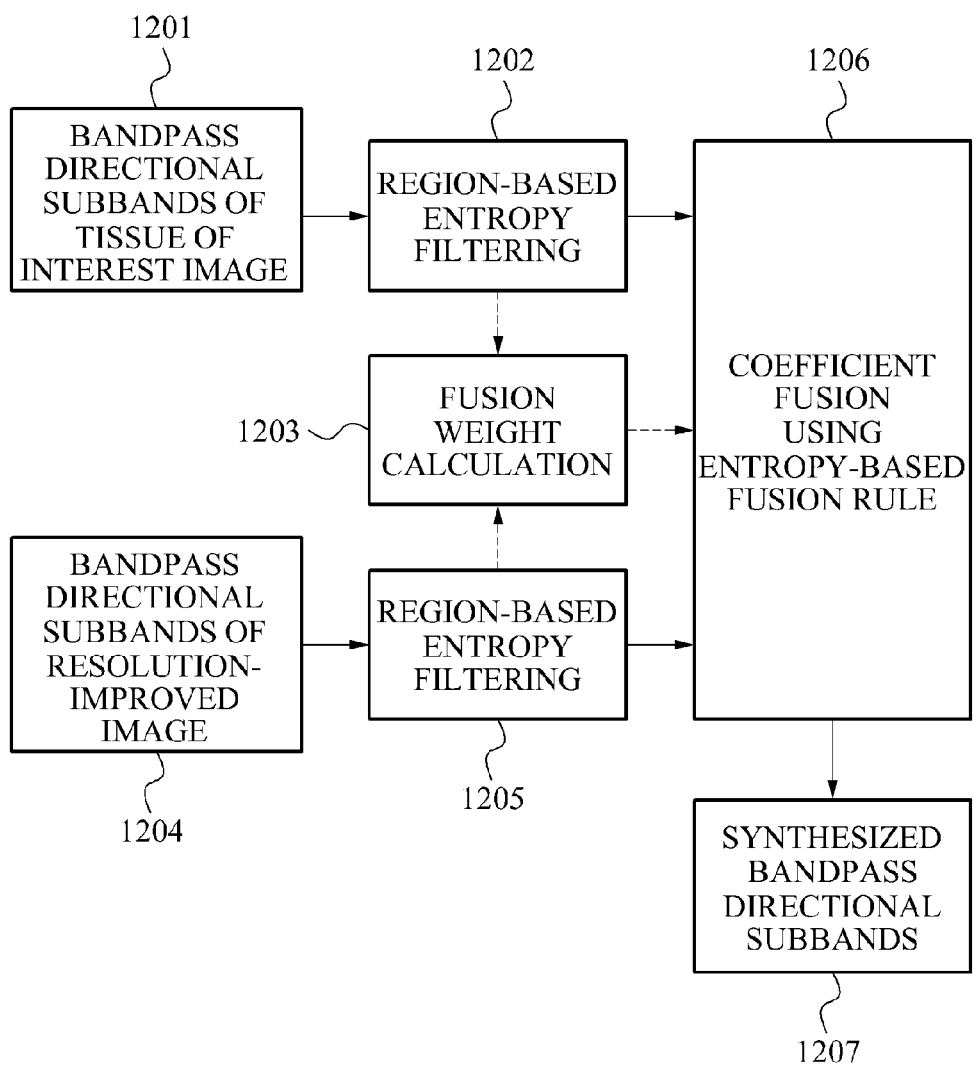
FIG. 12 is a diagram illustrating a process of a tissue of interest synthesis image generator synthesizing a coefficient of a high-pass component according to an exemplary embodiment.

FIG. 11 is a diagram illustrating a process of a second synthesis image generator synthesizing a coefficient of a low-pass component according to an exemplary embodiment, and FIG. 12 is a diagram illustrating a process of a second synthesis image generator synthesizing a coefficient of a high-pass component according to an exemplary embodiment.

Referring to FIG. 11, a low-pass subband 1101 of a tissue of interest image in a synthesis of a resolution improvement and noise reduction processed image with a plurality of image data in which a tissue of interest is highlighted may correspond to a spatial-domain fusion technique of synthesizing low-pass data of an ROI-highlighted image using a weighted average of pixel units.

In particular, the second synthesis image generator may enhance a contrast of the low-pass subband 1101 of the tissue of interest image in operation 1102, compute a fusion weight in operation 1103, and perform synthesis on a pixel basis through a weighted average fusion 1105.

In addition, the second synthesis image generator may add a low-pass subband 1104 of a resolution-improved image as an input of the weighted average fusion 1105, thereby outputting a synthesized low-pass subband 1106.

Referring to FIG. 12, an entropy-based fusion rule indicating an average amount of information of image data may be applied to bandpass directional subbands corresponding to a high-pass component.

In particular, the second synthesis image generator may compute a weight based on a region-based entropy filtering value to generate the fusion rule, and perform a coefficient synthesis.

The second synthesis image generator may generate second image data, by applying the entropy-based fusion rule indicating the average amount of information of the image data with respect to the high-pass component of the image data.

The second synthesis image generator may perform region-based entropy filtering 1202 with respect to bandpass directional subbands 1201 of a tissue of interest image, and input a result of performing the region-based entropy filtering 1202 into a coefficient fusion 1206 to which the entropy-based fusion rule is applied.

In addition, the second synthesis image generator may compute a fusion weight for a result of performing the region-based entropy filtering 1202, in operation 1203, and input a result of the computing into the coefficient fusion 1206 to which the entropy-based fusion rule is applied.

Further, the second synthesis image generator may perform a region-based entropy filtering 1205 with respect to bandpass directional subbands 1204 of a resolution-improved image, and input a result of performing the region-based entropy filtering 1205 into the coefficient fusion 1206 to which the entropy-based fusion rule is applied.

As another example, the second synthesis image generator may perform the region-based entropy filtering 1205 with respect to the bandpass directional subbands 1204 of the resolution-improved image, compute a fusion weight in operation 1203, and input a result of the computing into the coefficient fusion 1206 to which the entropy-based fusion rule is applied.

The second synthesis image generator may output synthesized bandpass directional subbands 1207 through the coefficient fusion 1206 to which the entropy-based fusion rule is applied.

Figure 13A:
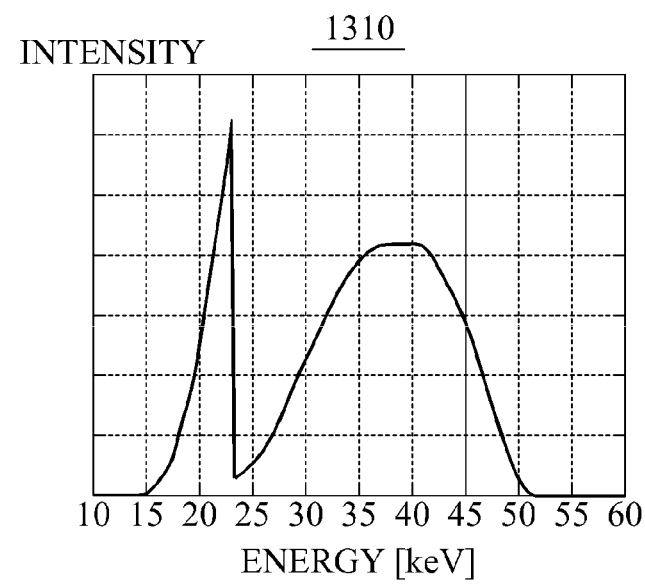
FIGS. 13A and 13B are graphs illustrating an image generating process of a spectral image generator according to an exemplary embodiment.
Figure 13B:
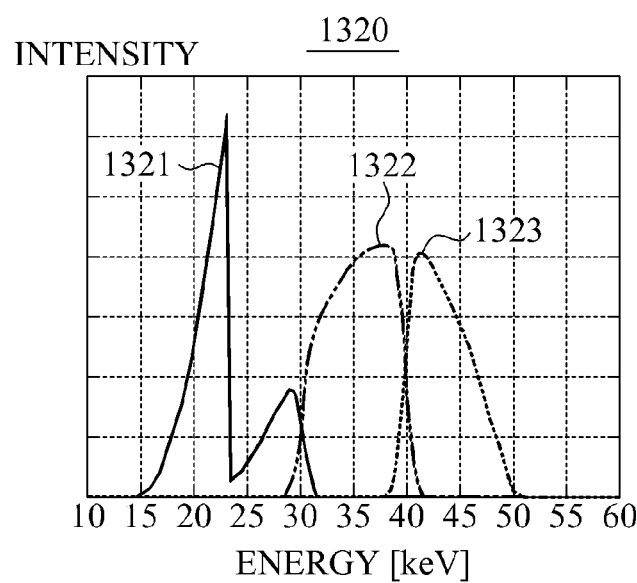

FIGS. 13A and 13B are graphs illustrating an image generating process of a spectral image generator according to an exemplary embodiment.

The spectral image generator may generate second image data, by performing at least one of a resolution improvement processing and a noise reduction processing with respect to a plurality of image data, respectively, synthesizing the processed plurality of image data, and converting the synthesized plurality of image data into a color image.

When a predetermined number of image data sets, for example, three image data sets, are input, the spectral image generator may generate color image data of a red channel, color image data of a green channel, and color image data of a blue channel, respectively corresponding to the input image data, using a low spectrum 1321, a mid-spectrum 1322, and a high spectrum 1323, in sequential order starting from a high energy band, as shown in a graph 1320 of FIG. 13B.

In particular, a first synthesis image generator may generate first image data in grayscale, and the spectral image generator may generate the second image data in color.

The spectral image generator may generate the second image data by synthesizing the generated color image data.

A spectral image display may alternately display the generated second image data and a grayscale full image generated through a full spectrum, as shown in a graph 1310 of FIG. 13A.

Figure 14A:
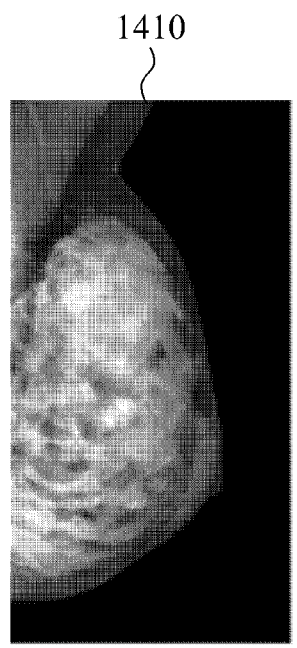
FIGS. 14A, 14B, and 14C are diagrams illustrating results of generating a resolution-improved image, an ROI image, and an output synthesis image in which an ROI is highlighted according to an exemplary embodiment.
Figure 14B:
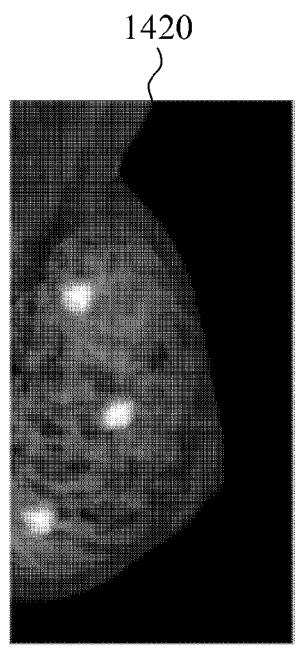
Figure 14C:
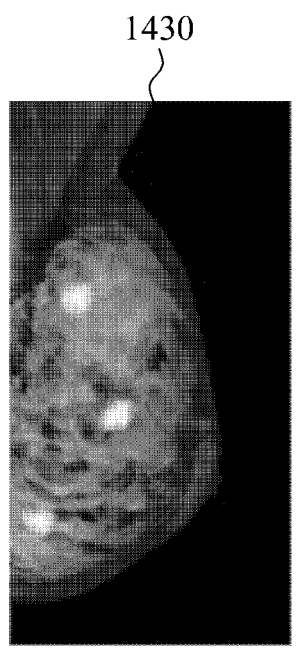

FIGS. 14A through 14C are diagrams illustrating an example of synthesizing a resolution-improved image 1410 with an ROI image 1420 in which an ROI is highlighted to generate a synthesis image 1430 in which an ROI is highlighted according to an exemplary embodiment.

According to an exemplary embodiment, an image in which an ROI, for example, a mass, is highlighted may be acquired in a medical imaging system using a MEX. Accordingly, a doctor or a medical specialist may readily perform diagnosis and disease determination, for example, whether a lesion exists, a size of the lesion, a position of the lesion, and the like.

In addition, a resolution-improved image having a characteristic identical to a characteristic of a related art diagnostic image, and an image generated by a MEX synthesis image generator may be alternately displayed on a display according to a change in time, and an image generated by a MEX color synthesis image generator may be displayed on a color display.

FIG. 15 is a flowchart illustrating a medical image processing method according to an exemplary embodiment.

In operation 1501, a MEX may be irradiated to an object, and an image generated when the MEX passes through the object may be detected, whereby a plurality of image data corresponding to a plurality of energy bands may be generated.

In operation 1502, at least one of a resolution improvement processing and a noise reduction processing may be performed with respect to the generated image data.

In particular, high quality first image data may be generated, by synthesizing the image data on which the at least one of the resolution improvement processing and the noise reduction processing is performed.

In operation 1503, a tissue of interest classified based on a predetermined characteristic may be highlighted to be distinguished from a normal tissue, with respect to the generated image data.

In particular, image data on which at least one of the resolution improvement processing and the noise reduction processing is performed may be synthesized with image data in which the tissue of interest is highlighted.

In operation 1504, first image data in which the tissue of interest is not highlighted, and second image data in which the tissue of interest is highlighted, among the plurality of image data, may be alternately displayed based on a predetermined criterion.

The medical image processing method according to the above-described exemplary embodiments may be recorded in computer-readable media including program instructions to implement various operations embodied by a computer. The media may also include, alone or in combination with the program instructions, data files, data structures, and the like. Examples of computer-readable media include magnetic media such as hard disks, floppy disks, and magnetic tape; optical media such as CD ROM disks and DVDs; magneto-optical media such as optical disks; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules in order to perform the operations of the above-described exemplary embodiments, or vice versa.

According to exemplary embodiments, there is provided a medical image processing apparatus and method that may increase a resolution of a portion of an image acquired using MEX, highlight a tissue of interest for the portion of the acquired image, and display a final diagnostic image, thereby facilitating a lesion diagnosis.

Although a few exemplary embodiments have been shown and described, exemplary embodiments are not limited thereto. Instead, it would be appreciated by those skilled in the art that changes may be made to the exemplary embodiments without departing from the principles and spirit of the disclosure, the scope of which is defined by the claims and their equivalents.

What is claimed is:

1. A medical image processing apparatus comprising:
   an image data generator which generates a first energy image data and a second energy image data respectively corresponding to two different energy bands using an X-ray;
   a region of interest (ROI) processor which receives and processes the first energy image data and the second energy image data to generate a highlighted first energy image data and a highlighted second energy image data, by highlighting tissue of interest classified based on a predetermined characteristic to be distinguished from a normal tissue;
   a resolution improvement and noise reduction processor configured to receive and process the first energy image data and the second energy image data to generate a contrast-improved first energy image data and a contrast-improved second energy image data, by performing at least one of a resolution improvement processing and a noise reduction processing;
   a first synthesis image generator configured to generate first image data, by synthesizing the contrast-improved first and second energy image data;
   a second synthesis image generator configured to generate second image data, by synthesizing the contrast-improved first and second energy image data with the highlighted first and second energy image data, in which the tissue of interest has been highlighted prior to the performing at least one of the resolution improvement processing and the noise reduction processing; and a display which alternately displays the first image data in which the tissue of interest is not highlighted, and the second image data in which the tissue of interest is highlighted to be distinguished from the normal tissue.

2. The apparatus of claim 1, wherein the second synthesis image generator generates the second image data by multi-scaling the image data on which at least one of the resolution improvement processing and the noise reduction processing is performed, and the image data in which the tissue of interest is highlighted, respectively, converting the multi-scaled image data into multi-directional information, performing at least one of a coefficient synthesis of a low-pass component and a coefficient synthesis of a high-pass component, on the image data converted into the multi-directional information, and reconstructing a result of the synthesizing through inverse contourlet transform (ICT).

3. The apparatus of claim 2, wherein the second synthesis image generator generates the second image data by applying a weight to the low-pass component on a pixel by pixel basis.

4. The apparatus of claim 2, wherein the second synthesis image generator generates the second image data by applying an entropy-based fusion rule to the high-pass component, and
   the entropy-based fusion rule indicates an average amount of information of the image data.

5. The apparatus of claim 1, wherein the ROI processor changes a brightness of the tissue of interest such that the tissue of interest is highlighted in comparison to the normal tissue.

6. The apparatus of claim 1, the ROI processor changes a color of the tissue of interest such that the tissue of interest is highlighted in comparison to the normal tissue.

7. The apparatus of claim 5, wherein the ROI processor processes the normal tissue to be displayed in grayscale for the tissue of interest to be highlighted in comparison to the normal tissue.

8. A medical image processing method comprising:
generating a first energy image data and a second energy image data respectively corresponding to two different energy bands by imaging an object using a wide-band energy X-ray;
receiving and processing the first energy image data and the second energy image data to generate a contrast-improved first energy image data and a contrast-improved second energy image data, by performing at least one of a resolution improvement processing and a noise reduction processing;
receiving and processing the first energy image data and the second energy image data to generate a highlighted first energy image data and a highlighted second energy image data, by highlighting a tissue of interest classified based on a predetermined characteristic to be distinguished from a normal tissue;
generating first image data, by synthesizing the contrast-improved first and second energy image data; and
generating second image data, by synthesizing the contrast-improved first and second energy image data with the highlighted first and second energy image data, in which the tissue of interest has been highlighted prior to the performing at least one of the resolution improvement processing and the noise reduction processing; and
alternately displaying the first image data in which the tissue of interest is not highlighted, and the second image data in which the tissue of interest is highlighted to be distinguished from the normal tissue.

9. A non-transitory computer-readable medium having recorded thereon a program which when executed by a computer causes the computer to perform the method of claim 8.

* * * * *